United States Patent [19]

Gallagher et al.

[11] 4,083,837

[45] Apr. 11, 1978

[54] OXIDATION OF HYDRAZONES TO THE CORRESPONDING DIAZO COMPOUND

[75] Inventors: Gerard Gallagher, Barrow-in-Furness; Derek Walker, Windermere, both of England

[73] Assignee: Glaxo Laboratories Limited, Greenford, England

[21] Appl. No.: 721,330

[22] Filed: Sep. 7, 1976

Related U.S. Application Data

[63] Continuation of Ser. No. 377,223, Jul. 9, 1973, abandoned.

[30] Foreign Application Priority Data

Jul. 11, 1972 United Kingdom .............. 32423/72

[51] Int. Cl.$^2$ ................. C07C 113/00; C07C 113/02; C07C 113/04
[52] U.S. Cl. ............................ 260/141; 260/239 AA; 260/239.1; 544/3; 560/250
[58] Field of Search ......................... 260/141, 239 AA

[56] References Cited

U.S. PATENT DOCUMENTS 3,488,342 1/1970 Sheppard et al. .................... 260/192

OTHER PUBLICATIONS

Houben-Weyl, "Methoden der Organischen Chemie," vol. 10/4, pp. 568-577, (1968).
Miller, J. Org. Chem., vol. 24, pp. 560-561, (1959).
Morrison, et al., J. Org. Chem., vol. 26, pp. 2617-2618, (1961).
Day, et al., Chemical Abstracts, vol. 64, 9577d, (1966).
Nenitzescu, et al., "Organic Synthesis," Collective vol. II, pp. 496-497, (1943).
Smith "Open-Chained Nitrogen Compounds," vol. 2, pp. 165-166, (1966).
Smith, et al., Organic Syntheses, Collective vol. III, pp. 351-352, (1955).
Theilheimer (I), "Synthetic Methods of Organic Chemistry," vol. 16, p. 172, (1962).
Theilheimer (II), "Synthetic Methods of Organic Chemistry," vol. 19, p. 155, (1965).

*Primary Examiner*—Floyd D. Higel
*Attorney, Agent, or Firm*—Bacon & Thomas

[57] ABSTRACT

A process for the preparation of diazo compounds, particularly diazoalkanes, is described in which a hydrazone is oxidized with an oxidizing agent, said oxidizing agent comprising an organic peracid, chloramine-T or N-chlorosuccinimide to a corresponding diazo compound, preferably in the presence of a base. The reaction may be catalyzed by an oxidation catalyst such as iodine.

13 Claims, No Drawings

OXIDATION OF HYDRAZONES TO THE CORRESPONDING DIAZO COMPOUND

This is a continuation, of application Ser. No. 377,223, filed July 9, 1973 now abandoned.

This invention relates to a process for the preparation of diazo compounds.

There is a growing need for efficient esterification processes which can be applied to sensitive organic acids without disturbing their molecular geometry, i.e., without molecular disruption or molecular rearrangements such as isomerization and racemization. Such processes are particularly needed in the manufacture of cephalosporin and penicillin antibiotics where it is frequently necessary to protect a carboxyl group by esterification to enable chemical transformations to be carried out elsewhere in the molecule.

One class of esterifying agents which has been found particularly useful in the treatment of sensitive organic acids comprises diazoalkanes, in particular diazomethane and substituted diazomethanes, which react with the acid to give the methyl or substituted methyl ester respectively, often in near-stoichiometric yield. Although such esterifying agents are widely employed on a laboratory scale, the lack of a commercially acceptable method of preparing appropriate diazoalkanes has prevented their use in industrial scale esterification processes.

The most commonly used current methods of preparing diazo compounds such as diazoalkanes comprise the treatment of N-alkyl-N-nitroso ureas and sulphonamides with base and the oxidation of aldehydic and ketonic hydrazones with oxidising agents such as mercuric oxide, manganese dioxide, nickel peroxide, silver oxide and lead tetraacetate. The former method is disadvantageous in that the N-nitroso compounds employed are frequently unstable and difficult to store and in several cases exhibit carcinogenic properties. The oxidative preparations are preferred in that relatively stable, accessible materials are involved, but suffer the disadvantage that the oxidising agents are expensive and in most cases require careful preparation to ensure that they exhibit reproducible activity. Also, in some cases undesirably large quantities of the oxidising agent are required.

Since in addition to exihibiting useful esterifying properties diazoalkanes are valuable alkylating agents there is a need for a convenient and efficient process for their preparation. We have now found that diazo compounds such as diazo alkanes can be prepared by treatment of hydrazones with certain commercially acceptable oxidising agents in the presence of a base, or, when the oxidation reaction is effected at low temperatures, followed by treatment with a base.

Thus according to one aspect of the invention we provide a process for the preparation of a diazo compound of the formula

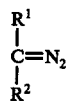

(where $R^1$ is a hydrogen atom or R, where R is an aryl, aralkyl, 5- or 6-membered heterocyclic, heterocyclic-substituted alkyl, alkyl or cycloalkyl group, which groups are unsubstituted or substituted by one or more halogen atoms or cyano, nitro, alkyl, alkylsulphonyl or alkoxy groups; $R^2$ has independently any of the defined meanings for R; or where $R^1$ and $R^2$ together with the intervening carbon atom form a cyclic hydrocarbon group which may be interrupted by one or more of O or N) which comprises reacting a hydrazone of the formula

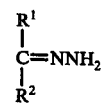

(where $R^1$ and $R^2$ are as defined above) with an oxidising agent in the presence of a base, said oxidising agent comprising an organic peracid, a hypohalous acid, a hypohalite salt or ester, chlorine, bromine or chromic acid.

The oxidising agent may for example be an organic peracid such as peracetic acid or m-chloroperbenzoic acid; or a hypohalous acid or salt or ester thereof such as hypochlorous acid, sodium hypochlorite or t-butylhypochlorite. When the oxidation is effected by a halogen, this may for example be molecular chlorine or bromine; chlorine or bromine may also be used in an activated form, as in compounds which possess a source of positive halogen ions, such as an N-haloamide (e.g. an N-chloroamide such as N-chlorosuccinimide) or an N-halosulphonamide (e.g. an N-chloroarylsulphonamide such as chloramine-T or N-chlorosaccharin). Mixtures of the oxidising agents may also be used to advantage, e.g. a combination of a peracid and an N-bromoamide.

In other words, the oxidizing agent may be a member selected from the group consisting of organic peracid, chloramine-T and N-chlorosuccinimide and mixtures thereof.

If desired peracids may be formed in situ (e.g. from hydrogen peroxide and hexafluoroacetone).

Peracetic acid is a particularly preferred oxidising agent for use in the process.

The reaction is preferably effected in the presence of an oxidation catalyst, particularly when the oxidising agent is an organic peracid. Such catalysts may for example be iodine or an iodide (e.g. ammonium iodide or a quaternary ammonium iodide) or an iodonium salt such as iodine bromide, a quinone (e.g. a benzoquinone such as tetrachlorobenzoquinone) or a metal cation (e.g. copper I or II, cobalt II or III, nickel II or manganese II, III or IV). The use of iodine or an iodide is particularly preferred in that advantageously higher yields of the desired diazo compound can be obtained.

The reaction is conveniently effected in an organic solvent, which is advantageously inert. Mixtures of solvents may also be used. Suitable solvents include chlorinated hydrocarbons, e.g. chloroform, 1,2-dichloroethane or methylene chloride; aromatic hydrocarbons, e.g. toluene or tetralin; aliphatic esters, e.g. ethyl acetate or butyl acetate; ketones, e.g. acetone or methyl isobutyl ketone; aliphatic hydrocarbons, e.g. n-hexane or cyclohexane; aliphatic and cyclic ethers, e.g. diethyl ether or tetrahydrofuran; nitriles, e.g. acetonitrile; and N,N-disubstituted amides, e.g. dimethylacetamide. The reaction may also be effected in a homogeneous aqueous reaction medium, e.g. mixture of water and ethanol or acetonitrile.

The reaction may alternatively be carried out in a mixture of water and a water immiscible organic solvent (e.g. a chlorinated hydrocarbon such as A phase transfer catalyst is preferably used in such circumstances, as is described in the copending United States application Ser. No. 377,248 of David Thomas Eastlick filed July 9, 1973, now abandoned.

The hydrazone (II) need not be completely dissolved in the solvent, although lower reaction rates may result if a significant proportion of the compound is out of solution. In such cases it may be convenient to mill crystals of the hydrazone to a fine particle size (e.g. c.10$\mu$) before oxidation in order to increase the reaction rate.

Both inorganic and organic bases may be used in the process; the base is preferably inert to the oxidising reaction conditions, but it need not necessarily be inert provided that the oxidation product of the base is itself capable of oxidising the hydrazone (II), preferably without loss of efficiency. Thus, for example, aqueous sodium hydroxide may be used as base together with chlorine as oxidising agent, since the resulting sodium hypochlorite will itself oxidise the hydrazone. Excess base should normally be employed in such circumstances to allow for consumption of base by the oxidising agent.

In general, inorganic bases which may be used include alkali metal and alkaline earth metal hydroxides, bicarbonates and carbonates, e.g. sodium or potassium hydroxide, bicarbonate or carbonate, or calcium carbonate. Where an inorganic base is employed, the reaction may be carried out in an aqueous medium such as described above, the base being dissolved or suspended in the medium. The use of an inorganic base is generally preferred for economic considerations.

Organic bases for use in the process are desirably substantially inert to the oxidising conditions, since such bases will generally not react to give a further oxidising species. Thus suitable organic bases include guanidines such as tetramethylguanidine, quaternary ammonium hydroxides such as tetra-n-butylammonium hydroxide, basic amides such as dimethylacetamide or resins with non-oxidisable basic groups e.g. quaternary ammonium resins, either in hydroxide or salt (e.g. carbonate) form. Such bases may generally be employed in solution or suspension in the organic solvent and water may be excluded from the reaction system. It is usually convenient to use a water-soluble organic base which can be removed after the oxidation by aqueous washing.

In other words, the base may be an alkali metal or alkaline earth metal hydroxide, bicarbonate or carbonate, a guanidine a basic amide, a quaternary ammonium hydroxide, pyridine, quinoline, tetramethylpiperidine, or triethyl amine.

It will be appreciated that when the oxidising agent is itself a base (e.g. cloramine-T) the presence of an additional base may be unnecessary.

The oxidation reaction is exothermic and may for example be effected at a temperature in the range $-50°$ to $+100°$ C, preferably $-15°$ to $+30°$ C. The temperature will to some extent depend on the nature of the hydrazone employed.

The course of the reaction may be followed using infra-red spectroscopy, e.g. by monitoring the strong absorption in the region 2,030–2,080 cm$^{-1}$ characteristic of diazoalkanes. Alternatively, ultraviolet spectroscopy may be employed, and is particularly suitable in many cases for the quantitative determination of the yield of diazo compound. In some cases it is possible to follow the course of the reaction using thin layer chromatography, a technique which is valuable in assessing whether any unreacted hydrazone is present. The amount of diazo compound produced can also be determined by acidification and measurement of the amount of nitrogen evolved.

The process is conveniently carried out by adding the oxidising agent to a mixture of the hydrazone (II) and the base (and, where appropriate, the oxidation catalyst) in solution or suspension in the medium, the rate of addition of the oxidising agent and the thermal control preferably being such as to maintain the temperature of the reaction mixture in the range $-50°$ to $+100°$ C. Other modes of addition may also be employed, however; thus, for example, the base and the oxidising agent may be added simultaneously and equivalently to a solution of the hydrazone. Alternatively, the base and the oxidising agent may be pre-mixed, preferably at low temperature, and added to a solution or suspension of the hydrazone (and, where appropriate, the oxidation catalyst). Where the various components are brought together in organic solvents it is preferred that the solvents should be the same.

The reaction is conveniently effected using 0.5–2.0, e.g. 0.9–1.5, moles of oxidising agent and 0.5–10, e.g. 0.9–5.0, moles of base per mole of hydrazone. Generally the preferred range is 1.0 to 1.4 moles of oxidising agent and sufficient base to neutralise all the acid present or produced. When a water/water-immiscible organic solvent system is used it is advantageous to add base simultaneously and equivalently with the oxidising agent so as to maintain a pH of about 10.

When an oxidation catalyst is used, the required level is generally very low, usually from $10^{-1}$ to $10^{-6}$, preferably from $10^{-2}$ to $10^{-4}$ moles per mole of hydrazone.

A wide range of hydrazones may be employed in the process, these being prepared by, for example, standard methods starting from aldehydes and ketones, e.g. reaction of a compound $R^1R^2CO$ (where $R^1$ and $R^2$ have the above-defined meanings) with hydrazine. Thus in the above formula I and II $R^1$ and/or $R^2$ may be alkyl groups preferably containing 1–6 carbon atoms, such as methyl, ethyl, n-propyl, isopropyl etc.; cycloalkyl groups which may contain 5–7 carbon atoms in the ring, e.g. cyclopentyl, cyclohexyl; aryl groups such as phenyl, naphthyl etc.; aralkyl groups, which are preferably monocyclic and contain 1–6 carbon atoms in the alkyl portion, such as benzyl; 5- or 6- membered heterocyclic rings containing one or more atoms of O, N and S, e.g. 2-thienyl, 2-furyl, 2-pyridinyl etc.; heterocyclic-substituted alkyl groups, preferably containing 1–6 carbon atoms in the alkyl portion, e.g. 2-thienylmethyl, 2-furylmethyl etc.; or any of the above groups substituted by one or more halogen atoms, cyano, nitro, alkyl, alkylsulphonyl or alkoxy groups, these last preferably containing 1–6 carbon atoms, such as methyl, ethyl, n-propyl, isopropyl, ethoxy, isopropoxy or methylsulphonyl. The hydrazones may also possess a further hydrazone group. The aralkyl, alkyl, cycloalkyl and heterocyclic groups may be unsaturated.

Alternatively $R^1$ and $R^2$ may, together with the attached carbon atoms form a cyclic structure, e.g. cyclopentyl, cyclohexyl, 9-fluorenyl, pyranyl or piperidinyl.

In other words, $R^1$ is selected from the group consisting of hydrogen and R, where R is phenyl, naphthyl, benzyl, thienyl, furyl, pyridinyl, thienylmethyl, furylmethyl, $C_{1-6}$ alkenyl, $C_{5-7}$ cycloalkenyol, $C_{1-6}$ alkyl and $C_{5-7}$ cycloalkyl groups and such groups substituted by at least one of chloro, bromo, cyano, nitro, $C_{1-6}$ alkyl, $C_{1-6}$ alkylsulphonyl, and $C_{1-6}$ alkoxy; $R^2$ has independently any of the defined meanings for R; or where $R^1$ and $R^2$ together with the intervening carbon atom form a member selected from the group consisting of cyclopentyl, cyclohexyl, fluorenyl, pyranyl and piperidinyl.

As indicated above, the diazo compounds prepared by the process of the invention are useful agents for the esterification of sensitive organic acids and may, for example, be used to introduce easily removable ester groups into compounds such as penicillins and cephalosporins. Compounds of formula I useful for this purpose include those in which $R^1$ and $R^2$ are such that the resulting ester grouping $R^1R^2CH-$ is an aralkyl group containing 1 or 2 carbocyclic or heterocyclic aryl groups attached to the C 1 atom of a lower ($C_{1-6}$) alkyl portion, e.g. benzyl, diphenylmethyl, 2-furylmethyl, di(2-thienyl)methyl, phenyl(2-thienyl) methyl or 9-fluorenyl; a cycloalkyl group such as cyclopentyl; or a substituted version of any of these groups, e.g. p-nitrobenzyl or di(p-methoxyphenyl)methyl. This list is now however, intended to be exhaustive.

While we do not wish to be bound by theoretical considerations it is believed that the presence of base enhances the yield of diazo compound by binding any acids present in or produced by the oxidising agent which would otherwise tend to react with the diazo compound leading to its decomposition. The base is also thought to moderate the oxidation reaction, reducing any tendency for the diazo compound to be oxidised further to, for example, corresponding carbonyl derivatives.

In certain cases, e.g. when low reaction temperatures, such as in the range $-50°$ to $-20°$ C, are employed to moderate the reaction rate, it may be possible to dispense with the presence of the base during oxidation of the hydrazone, base being added subsequently to stabilise the diazo product. Such modified reaction procedures comprise a further feature of the invention.

It will be appreciated from the foregoing that the invention also includes a process for the preparation of a diazo compound which comprises reacting the corresponding hydrazone with an oxidising agent in the presence of a base and a catalyst comprising iodine, an iodide or an iodonium salt. In this process any hydrazone capable of being oxidised to a diazo compound may be used, and similarly any suitable oxidising agent may be used. Examples of suitable hydrazones and oxidising agents include those referred to above.

The following Examples serve to illustrate the invention.

In Examples 1-4 formation of the diazo compound was determined by the appearance of a magenta colour, by showing the presence of the characteristic absorption spectrum of diphenyldiazomethane in the ultraviolet, by appearance of the characteristic stretching frequency for the diazoalkane group in the infra red and by the evolution of nitrogen on the addition of acid. All temperatures are in ° C.

PREPARATIONS OF DIPHENYLDIAZOMETHANE

EXAMPLE 1

To a mixture of benzophenone hydrazone (8.8 g; 0.05 mole) and sodium bicarbonate (12.9 g; 0.1535 mole) in aqueous acetone (300 ml of a 1:2 mixture) stirred and cooled to 15° was added peracetic acid (8.85 ml of a 38% w/w solution in glacial acetic acid; 0.05 mole) during sixty minutes, the temperature being maintained at 15° throughout.

The reaction mixture was diluted with water (200 ml) and the product extracted into diethyl ether (2 × 100 ml) the ethereal extracts being washed sequentially with water (50 ml). The red ethereal extracts contained diphenyldiazomethane. The solution was used in the preparation of penicillin G 1$\beta$-oxide diphenylmethyl ester, the characteristics of which conformed to an authentic sample.

EXAMPLE 2

To a mixture of benzophenone hydrazone (19.6 g; 0.1 mole) and pyridine (49.6 ml; 0.614 mole) in ether (100 ml) stirred and cooled to 15° was added peracetic acid (17.7 ml of a 38% w/w solution in glacial acetic acid; 0.1 mole) during 45 minutes, the temperature being maintained at +15° throughout.

The reaction mixture was washed with water (2 × 100 ml), the aqueous phases being backwashed sequentially with ether (150 ml).

EXAMPLE 3

To a mixture of benzophenone hydrazone (19.6 g; 0.1 mole) and quinoline (36.4 ml; 0.307 mole) in ether (100 ml) stirred and cooled to 15° was added peracetic acid (17.7 ml of a 38% w/w solution in glacial acetic acid; 0.1 mole) during 60 minutes, the temperature being maintained at +15° throughout.

The reaction mixture was washed with water (2 × 200 ml) the aqueous phases being backwashed sequentially with ether (50 ml).

EXAMPLE 4

PREPARATION OF PHENYL-2-THIENYLDIAZOMETHANE

To a mixture of phenyl-2-thienyl ketone hydrazone (20.2 g; 0.1 mole), and pyridine (24.8 ml; 0.307 mole) in N,N-dimethylacetamide (100 ml) stirred and cooled to 15° was added peracetic acid (17.7 ml of a 38% w/w solution in glacial acetic acid; 0.1 mole) during 40 minutes, the temperature being maintained at +15° throughout.

The reaction mixture was diluted with water (200 ml) and the product extracted with ether (3 × 100 ml), the ethereal extracts being washed sequentially with water (100 ml).

The solution obtained in Examples 1 to 4 may be evaporated to provide the solid diazo compound, but this is of course unnecessary if the diazo compound is to be used directly in for example esterification processes.

EXAMPLE 5

(2-Methylphenyl) phenyldiazomethane

To (2-methylphenyl)phenyl ketone hydrazone (10.5 g, 0.05 moles) dissolved in 1,2-dichloroethane (50 ml) containing iodide (2 ml, 1% w/v solution) and 1,1,3,3-tetramethylguanidine (22.5 ml) was added peracetic acid solution (11.4 ml, 1.27 × 0.05 moles) at 0° over 30 minutes. After the addition the mixture was stirred for 5 minutes longer. The red solution was washed with water (5 × 200 ml), dried over sodium sulphate and made up to 250 ml in a volumetric flask. An aliquot (50 ml) treated with excess acetic acid yielded 221 ml gas corrected to NTP which corresponded to a 98.6% yield of diazoalkane. The compound was characterised by a major absorption at 2050 cm$^{-1}$ and $\lambda_{max}$ 516 nm. A solid ester derivative was made by treating (5R, 6R, 1S, 3S)-2,2-dimethyl-6-phenylacetamidopenam-3-carboxylic acid 1-oxide in chloroform with an aliquot of the diazoalkane solution. After gas evolution had ceased the slightly yellow solution was washed with 5% sodium bicarbonate solution, water, and the organic residue left after removal of the organic solvent crystallised from hot propan-2-ol. The solid was identified as (2-methylphenyl)phenylmethyl (5R, 6R, 3S, 1S)-2,2-dimethylpenam-6-phenylacetamidopenam-3-carboxylate 1-oxide by its n.m.r. spectrum and melting point and mixed melting point 140° - 145° with an authentic sample of the ester.

EXAMPLE 6

Phenyl (2-thienyl) diazomethane

To phenyl (2-thienyl) ketone hydrazone (10.1 g, 0.05 moles) dissolved in 1,2-dichloroethane (50 ml) containing iodine (2 ml, 1% w/v solution) and 1,1,3,3-tetramethylguanidine (22.5 ml) was added peracetic acid solution (11.4 ml, 1.27 × 0.05 moles) at 0° over 30 minutes followed by an additional stir time of 5 minutes. The red solution was washed with water (5 × 200 ml), dried over sodium sulphate and made up to 250 ml in a volumetric flask. An aliquot (50 ml) treated with excess acetic acid yielded 187 ml gas corrected to NTP which corresponded to a 83.4% yield of diazoalkane.

The compound was characterised by a major absorption at 2050 cm$^{-1}$, $\lambda_{max}$ 526 nm and by the crystalline ester prepared from (5R, 6R, 3S, 1S)-2,2-dimethyl-6-phenylacetamidopenam-3-carboxylic acid 1-oxide as described in Example 5, melting point and mixed melting point of 130° - 134° with an authentic sample. The n.m.r. spectrum of the prepared ester was consistent with its structure and showed no impurities save a little propan-2-ol.

EXAMPLE 7

(2-Furyl)diazomethane

To 2-furfuraldehyde hydrazone (5.5 g, 0.05 moles) in 1,2-dichloroethane (50 ml) containing iodine (2 ml, 1% w/v solution) and 1,1,3,3-tetramethylguanidine (26.4 ml) was added peracetic acid solution (11.4 ml, 1.27 × 0.05 moles) over 30 minutes at −20°. The mixture was stirred for 5 minutes longer during which time the slow evolution of gas continued. The orange-red solution was washed with ice cold water (5 × 200 ml) and made up to 250 ml with cold 1,2-dichloroethane in a volumetric flask. An aliquot (50 ml) treated with excess acetic acid yielded 191 ml gas corrected to NTP which corresponded to a 85.4% yield of diazoalkane.

The compound was characterised by a major absorption at 2070 cm$^{-1}$, $\lambda_{max}$ 498 nm and by the crystalline ester prepared from (5R, 6R, 3S, 1S)-2,2-dimethyl-6-phenylacetamidopenam-3-carboxylic acid 1-oxide as described in Example 5, melting point and mixed melting point 143° - 146° with an authentic sample. The n.m.r. spectrum was consistent with its structure and showed no impurities.

In like manner cyclohexanone hydrazone was converted to diazocyclohexane.

EXAMPLE 8

Diphenyldiazomethane

To diphenyl ketone hydrazone (19.6 g, 0.1 moles) dissolved in dichloromethane (100 ml) containing iodine (4 ml, 1% w/v solution) and 1,1,3,3-tetramethylguanidine (45 ml) was added peracetic acid solution (23.5 ml, 1.30 × 0.05 moles) at 0° over 60 minutes. The mixture was stirred for an additional 15 minutes. The purple-red solution was washed with water (5 × 250 ml), dried and made up to 500 ml in a volumetric flask. A UV assay on a suitably diluted aliquot corresponded to a yield of diazoalkane of 95.6%.

The compound was characterised by a major absorption at 2050 cm$^{-1}$, $\lambda_{max}$ 525 nm and by the crystalline ester prepared from (5R, 6R, 3S, 1S)-2,2-dimethylpenam-6-phenylacetamidopenam-3-carboxylic acid 1-oxide as described in Example 5, melting point and mixed melting point 144° - 146° with an authentic sample. The n.m.r. spectrum of the prepared ester was consistent with its structure and showed no impurities.

EXAMPLE 9 p-Methoxypenzyldiazomethane

To p-methoxybenzaldehyde hydrazone (7.5 g, 0.05 moles) dissolved in 1,2-dichloroethane (50 ml) containing iodine (2 ml, 1% w/v solution) and 1,1,3,3-tetramethylguanidine (26.4 ml) was added peracetic acid solution (11.4 ml, 1.27 × 0.05 moles) at −20° over 30 minutes with an additional stir time of 5 minutes. The red solution was washed with ice cold water (5 × 200 ml) and made up to 250 ml in a volumetric flask. An aliquot (50 ml) treated with excess acetic acid yielded 172 ml gas corrected to NTP which corresponded to a yield of 76.8% of diazoalkane.

The compound was characterised by a major absorption at 2060 cm$^{-1}$, $\lambda_{max}$ 509 nm and by the crystalline ester prepared from (5R, 6R, 3S, 1S)-2,2-dimethyl-6-phenylacetamidopenam-3-carboxylic acid 1-oxide as described in Example 5, melting point 146° - 148° (reported m.pt. 149° - 150°). The n.m.r. spectrum of the prepared ester was consistent with its structure and showed no impurities.

EXAMPLE 10

Diphenyldiazomethane

To benzophenone hydrazone (9.8 g, 0.05 moles) in dichloromethane (100 ml) containing 1,1,3,3-tetramethylguanidine (7.00 ml) and iodine (2 ml, 1% w/v solution) was added solid m-chlorperbenzoic acid (8.62 g, 0.05 moles) over 8 minutes at 0°. The red-purple solution was stirred at 0° - 10° for 30 minutes before being washed with water (3 × 150 ml). A UV assay on a suitably diluted aliquot at 525 nm indicated a 89.9% yield of diazoalkane.

EXAMPLE 11

Diphenyldiazomethane

To benzophenone hydrazone (9.8 g, 0.05 moles) in dichloromethane (100 ml) containing iodine (2 ml, 1% w/v solution) was added peracetic acid (37.5% solution, 9.15 ml, 0.051 moles) dropwise over 15 minutes at −30°. The red solution was stirred for 5 minutes longer. Triethylamine (0.22 moles, 31 ml) was added at −30° and the temperature allowed to rise before washing with water (5 × 250 ml). A UV assay on a suitably diluted aliquot at 525 nm indicated a 44.6% yield of diazoalkane.

EXAMPLE 12

9-Diazofluorene

To 9-fluorenone hydrazone (9.7 g, 0.05 moles) in 1,2-dichloroethane (50 ml) together with 1,1,3,3-tetramethylguanidine (26.4 ml) and iodine (2 ml, 1% w/v solution) was added peracetic acid solution (11.4 ml, 1.27 × 0.05 moles) over 25 minutes at 10° – 15°. The orange solution was stirred for 15 minutes at 15°, washed with water (5 × 250 ml) and made up to 250 ml in a volumetric flask. An aliquot (50 ml) treated with excess acetic acid yielded 193 ml gas corrected to NTP which corresponded to a 86.2% yield of diazoalkane.

The compound was characterised by a major absorption at 2065 cm$^{-1}$, $\lambda_{max}$ 500 nm and by the crystalline ester prepared from (5R, 6R, 3S, 1S)-2,2-dimethyl-6-phenylacetamidopenam-3-carboxylic acid 1-oxide as described in Example 5, melting point and mixed melting point 154.5° – 157° with an authentic sample. The n.m.r. spectrum of the prepared ester was consistent with its structure and showed no impurities.

EXAMPLE 13

Phenyldiazomethane

To benzaldehyde hydrazone (5.95 g, 0.05 moles) in 1,2-dichloroethane (50 ml) containing 1,1,3,3-tetramethylguanidine (26.4 ml) and iodine (2 ml, 1% w/v solution) was added peracetic acid solution (11.4 ml, 1.27 × 0.05 moles) over 12 minutes at 0°. The red solution, which was gently evolving nitrogen, was stirred for 20 minutes at 0° to −5° before being washed with water (5 × 250 ml) and made up to 250 ml in a volumetric flask. An aliquot (50 ml) treated with excess acetic acid yielded 199 ml gas at NTP which corresponded to a yield of diazoalkane of 88.9%.

The compound was characterised by a major absorption at 2065 cm$^{-1}$, $\lambda_{max}$ 492 nm and by the crystalline ester prepared from (5R, 6R, 3S, 1S)-2,2-dimethyl-6-phenylacetamidopenam-3-carboxylic acid 1-oxide as described in Example 5, melting point and mixed melting point 147° – 148° with an authentic sample. The n.m.r. spectrum of the prepared ester was consistent with its structure and showed no impurities.

EXAMPLE 14

Diphenyldiazomethane

To benzophenone hydrazone (19.6 g, 0.1 mole) in dichloromethane (100 ml) containing 1,1,3,3-tetramethylguanidine (42.5 ml) and bromine (2.3 ml, 1.10% w/v solution) was added peracetic acid solution (19.5 ml, 1.1 × 0.1 moles) at 20° over 60 minutes. The red solution was stirred for a further 10 minutes before being washed with water (5 × 250 ml). A UV assay at 525 nm of a suitably diluted aliquot corresponded to a yield of 17% diazoalkane.

EXAMPLE 15

Diphenyldiazomethane

To benzophenone hydrazone (9.8 g, 0.05 moles) in dichloromethane (50 ml) containing iodine (2 ml, 1% w/v solution) and 1,1,3,3-tetramethylguanidine (6.6 ml, 0.05 moles) at 15° was added slowly over 30 minutes N-chlorosuccinimide. The reaction mixture was washed with water (5 × 200 ml) and made up to 250 ml in a volumetric flask. A UV assay at 525 nm of a suitably diluted aliquot corresponded to a yield of 76.5% of the diazoalkane.

EXAMPLE 16

Diphenyldiazomethane

To benzophenone hydrazone (9.8 g, 0.05 moles) in 50% aqueous acetonitrile (50 ml) containing 1,1,3,3-tetramethylguanidine (21.3 ml) and cupric sulphate (19.5 mgm, 7.25 × 10$^{-5}$ moles) was added peracetic acid solution (9.5 ml, 1.08 × 0.05 moles) at 20° over 60 minutes. The solution was stirred for 4 hours at 20° before being extracted with dichloromethane (2 × 100 ml) and the combined organic extracts washed with water (5 × 250 ml). A UV assay at 525 nm of a suitably diluted aliquot corresponded to a yield of 35% of diazoalkane.

EXAMPLE 17

2-Thiophenediazomethane

To 2-thiophene aldehyde hydrazone (6.3 g, 80% pure, 0.04 moles) in 1,2-dichloroethane (50 ml) containing iodine (2 ml, 1% w/v solution) and 1,1,3,3-tetramethylguanidine (26.4 ml) was added peracetic acid solution (11.4 ml, 1.58 × 0.04 moles) over 15 minutes at 0° to −5°. The solution, which was slowly evolving gas, was stirred for a further 15 minutes at −5° to 0° before being washed with ice cold water (5 × 250 ml) and made up to 250 ml in a volumetric flask. An aliquot (50 ml) of the dull-red solution on treatment with excess glacial acetic acid yielded 141 ml gas corrected to NTP which corresponded to a yield of 78.7% of diazoalkane.

The compound was characterised by a major absorption at 2067 cm$^{-1}$, $\lambda_{max}$ 505 nm and (by the crystalline ester prepared from (5R, 6R, 3S, 1S)-2,2-dimethyl-6-phenylacetamidopenam-3-carboxylic acid 1-oxide) m.pt. 159° – 160°. The infra red and n.m.r. spectra and microanalysis were consistent with its structure.

EXAMPLE 18

Phenylmethyldiazomethane

To acetophenone hydrazone (6.7 g, 0.05 moles) in 1,2-dichloroethane (50 ml) containing iodine (2 ml, 1% w/v solution) and 1,1,3,3-tetramethylguanidine (26.4 ml) was added peracetic acid solution (11.4 ml, 1.27 × 0.05 moles) over 20 minutes at −5°. The mixture was stirred for an additional 15 minutes at 0° before being washed with cold water (4 × 250 ml) and made up to 250 ml in a volumetric flask. An aliquot (25 ml) of the light-red solution on treatment with excess glacial acetic acid yielded 108 ml gas corrected to NTP which corresponded to a yield of 96% diazoalkane. The compound was characterised by a major absorption at 2040 cm$^{-1}$, $\lambda_{max}$ 519 nm and by the crystalline ester prepared from (5R, 6R, 3S, 1S)-2-2-dimethyl-6-phenylacetamidopenam-3-carboxylic acid 1-oxide, melting point and mixed melting point with an authentic sample of the ester 168° – 170.5°. The n.m.r. spectrum of the compound was consistent with its structure and showed no impurities.

EXAMPLE 19

Diphenyldiazomethane

To benzophenone hydrazone (9.25 g, 47.5 m. moles) contained in dichloromethane (55 ml) at 0° with iodine (1.9 ml, 1% w/v solution) and 2,2,6,6-tetramethylpiperidine (25 g, 0.18 moles) was added dropwise peracetic acid solution (10.7 ml, 1.27 × 47.5 m. moles) over 15 minutes. The solution was stirred for an additional 15 minutes before being washed with water (5 × 250 ml) and dried. A UV assay at 525 nm on a suitably diluted aliquot corresponded to a yield of 34.6% diazoalkane.

EXAMPLE 20

Diphenyldiazomethane

To benzophenone hydrazone (9.8 g, 0.05 moles) dissolved in dichloromethane (50 ml) containing iodine bromide (2 ml, 1% w/v solution) and 1,1,3,3-tetramethylguanidine (26.4 ml) was added peracetic acid solution (11.4 ml, 1.27 × 0.05 moles) at 10° over 20 minutes. The solution was stirred for an additional 10 minutes before being washed with water (5 × 250 ml) and dried. A UV assay at 525 nm on a suitably diluted aliquot corresponded to a yield of 93% diazoalkane.

EXAMPLE 21

Diphenyldiazomethane

To benzophenone hydrazone (19.6 g, 0.1 mole) contained in dimethylformamide (100 ml) together with iodine (4 ml, 1% w/v dichloromethane solution) and guanidine carbonate (75.8 g) was added peracetic acid solution (22.8 ml, 1.27 × 0.1 moles) over 60 minutes followed by a stir time of 60 minutes. The reaction mixture was poured into water (1.5 l) and washed in counter-current batch fashion with dichloromethane (200 ml and 3 × 50 ml) and water (3 × 250 ml). A UV assay at 525 nm on a suitably diluted aliquot corresponded to a yield of 60.5%.

EXAMPLE 22

Diphenyldiazomethane

To benzophenone hydrazone (4.9 g, 0.025 moles) in dimethylformamide (25 ml) containing iodine (1 ml, 1% w/v solution) and excess Dowex 1 × 2 quaternary ammonium hydroxide resin saturated with dimethyl formamide was added peracetic acid solution (5.7 ml, 1.27 × 0.025 m. moles) at 15° over 60 minutes.

Stirring was continued for an additional 10 minutes before filtering the mixture. The filtrate and dichloromethane washings from the resin were made up to 500 ml with dichloromethane in a volumetric flask. A UV assay at 525 nm on a suitably diluted aliquot corresponded to a yield of 41.5% diazoalkane.

EXAMPLE 23

Diphenyldiazomethane

To benzophenone hydrazone (9.8 g, 0.05 moles) in dimethylacetamide (100 ml) at −20° containing iodine (2 ml, 1% w/v solution in dichloromethane) was added peracetic acid solution (9.15 ml, 1.02 × 0.05 moles) over 30 minutes. The deep red purple solution was immediately poured into dichloromethane (150 ml). The organic layer was further washed with sodium bicarbonate solution (500 ml) followed by water (4 × 250 ml) and dried. A UV assay at 525 nm of a suitably diluted aliquot corresponded to a yield of 64.4% diazoalkane.

EXAMPLE 24

1,4-Bis(α-diazobenzyl) benzene

To 1,4-dibenzoylbenzene hydrazone (7.85 g, 25 m.moles) in 1,2-dichloroethane (50 ml) containing iodine (1 ml, 1% w/v solution) and 1,1,3,3-tetramethylguanidine (26.4 ml) was added peracetic acid solution (11.4 ml, 1.27 × 2 × 25 m. moles) at 0° over 45 minutes. All of the hydrazone gradually dissolved as the peracetic acid addition proceeded. After the addition the reaction was stirred for 5 minutes longer, washed with ice-cold water (5 × 250 ml) and made up to 500 ml in a volumetric flask. An aliquot (50 ml) treated with excess acetic acid yielded 80 ml gas corrected to NTP which corresponded to a 69.2% yield of the diazoalkane.

The compound was characterised by a major absorption at 2040 cm$^{-1}$, $\lambda_{max}$ 532 nm and by the crystalline 1,4-bis-(α-acetoxybenzyl) benzene ester m.p. 143° – 145° prepared by reaction with glacial acetic acid. The n.m.r. and i.r. spectra of the diacetate were compatible with its structure. The diazo compound exhibited pleochroism with polarised light and had m.p. 114° – 116° with decomposition. These properties are all in agreement with those reported by R. W. Murray and A. M. Trozzolo, J. Org. Chem. 1961, 26, 3109.

We claim:

1. A process for the preparation of a diazo compound of the formula:

where R$^1$ is selected from the group consisting of hydrogen and R, where R is phenyl, naphthyl, benzyl, thienyl, furyl, pyridinyl, thienylmethyl, furylmethyl, C$_{1-6}$ alkenyl, C$_{5-7}$ cycloalkenyl, C$_{1-6}$ alkyl and C$_{5-7}$ cycloalkyl groups and such groups substituted by at least one of chloro, bromo, cyano, nitro, C$_{1-6}$ alkyl, C$_{1-6}$ alkylsulphonyl, and C$_{1-6}$ alkoxy; R$^2$ has independently any of the defined meanings for R; or Where R$^1$ and R$^2$ together with the intervening carbon atom form a member selected from the group consisting of cyclopentyl, cyclohexyl, fluorenyl, pyranyl and piperidinyl which comprises reacting a hydrazone of the formula:

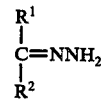

where R$^1$ and R$^2$ are as defined above with an oxidizing agent in the presence of an oxidation catalyst and a base, wherein 0.5–2.0 moles of oxidizing agent and 0.5–10 moles of base per mole of hydrazone is used; said base being an alkali metal or alkaline earth metal hydroxide, bicarbonate or carbonate, a guanidine, a basic amide, a quaternary ammonium hydroxide, pyridine, quinoline, tetramethylpiperidine, or triethyl amine, said oxidizing agent being a member selected from the group consisting of organic peracid, chloramine-T and N-chlorosuccinimide and mixtures thereof and said oxidation catalyst a member selected from the group consisting of iodine, an iodide and an iodonium salt.

2. A process as claimed in claim 1 wherein the oxidizing agent is an organic peracid.

3. A process as claimed in claim 1 wherein the oxidizing agent is N-chlorosuccinimide.

4. A process as claimed in claim 1 wherein the reaction is carried out in a mixture of water and a water immiscible organic solvent.

5. A process as claimed in claim 1, wherein the oxidation catalyst is present in an amount of $10^{-2}$ to $10^{-4}$ moles per mole of hydrazone.

6. A process as claimed in claim 1, wherein the amount of oxidation catalyst is from $10^{-2}$ to $10^{-4}$ moles per mole of hydrazone.

7. A process as claimed in claim 1 wherein the $R^1R^2C$-group is a benzyl, diphenylmethyl, 2-furylmethyl, (2-thienyl)methyl, phenyl (2-thienyl)methyl, 9-fluorenyl, p-nitrobenzyl or (p-methoxyphenyl)methyl group.

8. A process as claimed in claim 1 wherein the oxidising agent is peracetic acid.

9. A process as claimed in claim 1 wherein the oxidizing agent is chloramine.

10. A process as claimed in claim 1 which is effected at a temperature of $-15°$ to $+30°$ C.

11. A process as claimed in claim 1 wherein the base is an alkali metal of alkaline earth metal hydroxide, bicarbonate or carbonate.

12. A process as claimed in claim 1 wherein the base is a guanidine, a basic amide or a quaternary ammonium hydroxide.

13. A process for the preparation of a diazo compound of the formula:

where $R^1$ is selected from the group consisting of hydrogen and R, where R is phenyl, naphthyl, benzyl, thienyl, furyl, pyridinyl, thienylmethyl, furylmethyl, $C_{1-6}$ alkenyl, $C_{5-7}$ cycloalkenyl, $C_{1-6}$ alkyl and $C_{5-7}$ cycloalkyl groups and such groups substituted by at least one of chloro, bromo, cyano, nitro, $C_{1-6}$ alkyl, $C_{1-6}$ alkylsulphonyl, and $C_{1-6}$ alkoxy; $R^2$ has independently any of the defined meanings for R; or where $R^1$ and $R^2$ together with the intervening carbon atom form a member selected from the group consisting of cyclopentyl, cyclohexyl, fluorenyl, pyranyl and piperidinyl which comprises reacting at a temperature in the range of from $-50°$ C to $-20°$ C a hydrazone of the formula:

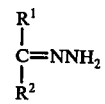

where $R^1$ and $R^2$ are as defined above with 0.5–2.0 moles of oxidizing agent per mole of hydrazone, selected from the group consisting of an organic peracid, N-chlorosuccinimide and chloroamine-T, and mixtures thereof in the presence of an oxidation catalyst and then subsequent to the stabilization of said diazo product a base selected from the group consisting of an alkali metal or alkaline earth metal hydroxide, bicarbonate or carbonate, a quanidine, a basic amide, a quaternary ammonium hydroxide, pyridine, quinoline, tetramethylpiperdine, and triethylamine is added in an amount of from 0.5–10 moles per mole of hydrazone, said oxidation catalyst selected from the group consisting of iodine, an iodide and an iodonium salt.

* * * * *